United States Patent de Cock

[11] Patent Number: 6,066,345
[45] Date of Patent: May 23, 2000

[54] ERYTHRITOL CONTAINING BEVERAGE IMPARTING A COOLING TASTE SENSATION

[75] Inventor: Petrus Wilhelmus Hubertus Antonius de Cock, Keerbergen, Belgium

[73] Assignee: Cerestar Holding B.V., Saas van Gent, Netherlands

[21] Appl. No.: 09/321,875

[22] Filed: May 28, 1999

[30] Foreign Application Priority Data

May 30, 1998 [GB] United Kingdom .................. 9811606

[51] Int. Cl.⁷ ................................ A23L 2/02; A23L 2/52; A23L 2/60; A23L 2/00; A23F 3/16
[52] U.S. Cl. .......................... 426/106; 426/131; 426/548; 426/590; 426/597; 426/599
[58] Field of Search ...................... 426/106, 131, 426/548, 590, 597, 599

[56] References Cited

FOREIGN PATENT DOCUMENTS

| 009 325 | 4/1980 | European Pat. Off. . |
| 792 589 | 9/1997 | European Pat. Off. . |
| 800 823 | 10/1997 | European Pat. Off. . |
| 1-034243 | 2/1989 | Japan . |
| 9-154483 | 6/1997 | Japan . |
| 10-136952 | 5/1998 | Japan . |
| 10-136953 | 5/1998 | Japan . |

OTHER PUBLICATIONS

Food Technology v. 49 Sep. 1995 C. 64–65+ (Dialog Abstract).
Soft Drinks Nanagement Int'l (Jun. '94) 28+30–31 (Dialog Abstract ).
J. of Liquid Chromatography 17(4) 855–865 (Dialog Abstract), 1994.
Database WPI Section Ch, week 9803 Derwent Publications Ltd., London, GB; Class B07, AN 98–022243 XP002087407 & JP 09 278671 28 Oct. 1997.

*Primary Examiner*—Steven Weinstein
*Attorney, Agent, or Firm*—Pillsbury Madison & Sutro LLP

[57] ABSTRACT

This invention relates to the use of erythritol to provide a cooling sensation in an orally used liquid product, to a beverage composition containing erythritol and to an oral care composition or a liquid pharmaceutical composition containing erythritol. The cooling effect comes in addition to the measurable effect which is due to the negative heat of dissolution and is most pronounced when the liquid product contains more than 7% w/v of erythritol.

3 Claims, No Drawings

ERYTHRITOL CONTAINING BEVERAGE IMPARTING A COOLING TASTE SENSATION

This invention relates to the use of erythritol to provide a cooling sensation in an orally used liquid product, to a beverage composition containing erythritol and to an oral care composition or a liquid pharmaceutical composition containing erythritol.

Many of the ready-to-drink beverages which are available on the market are intended for drinking when cooled to below room temperature. However, refrigeration is not always available to cool drinks to the temperature which is preferred for consumption. Drinking a beverage at room temperature, rather than in a cooled state, can have an adverse effect on the flavour and overall organoleptic properties of the beverage.

Similarly, oral care compositions (such as mouth wash) and liquid pharmaceutical compositions (such as cough syrups) are generally more acceptable to the user if they are cool or they impart a cooling sensation in the mouth.

Erythritol is known as an ingredient in beverages. For example, JP-A-7-274829 discloses tea drinks which contain 0.2 to 3 weight % of a sugar alcohol, such as erythritol, in order to reduce bitterness and astringency. JP-A-9-224588 and EP-A-0759273 describe the use of erythritol in amounts of 1.0 to 5.0 weight % and 0.2 to 3 weight %, respectively, to mask undesirable odours in vegetable and fruit juices. Calorie-reduced soft drinks containing aspartame and 0.1 to 5% w/v (weight by volume) erythritol are taught in EP-A-0792589; this document teaches that the erythritol acts to increase the storage stability of the soft drinks.

Thus, erythritol is conventionally included in beverages in amounts of up to about 5% by weight.

It is known that some polyols (including erythritol and xylitol) have a negative heat of solution. In practice this means that on dissolving a reasonable amount of erythritol in an aqueous liquid, the temperature of the liquid decreases measurably. This effect has been applied to produce powders which are dissolved in water to give a cool drink. For example, JP-A-63-258565 describes such a powder containing flavour or powdered fruit juice and 50 weight % or more erythritol. This document mentions reconstitution of the powders to produce an erythritol-containing drink. However, it teaches that the cooling effect is wholly due to the heat of dissolution of the erythritol and, for this reason, it contemplates packaged powdered beverages but not packaged beverages themselves. According to the teaching in JP-A-63-258565, there would be no advantage, in terms of cooling, in providing a packaged, ready-to-drink beverage because the heat of dissolution of the erythritol would not be available to provide a cooling effect.

The problem associated with the powders for reconstitution into beverages which are described in the prior art is that they require water (or another aqueous liquid) for reconstitution. Often, a source of water is simply not available. There remains, therefore, a need for a ready-to-drink beverage which has a cooling sensation.

The present invention solves this problem by identifying a previously unrecognised property of erythritol.

Accordingly, the present invention provides the use of erythritol in aqueous solution to provide a cooling sensation in an orally used liquid product. Preferably, the erythritol is present in the liquid product in an amount of more than 7% w/v (more preferably 7.5 to 25% w/v).

The invention also provides a packaged, ready-to-drink, flavoured beverage composition comprising more than 7% w/v erythritol and an oral care composition or liquid pharmaceutical composition comprising more than 7% w/v erythritol.

It has surprisingly been found that aqueous solutions of erythritol, particularly those containing more than 7% w/v erythritol, are perceived as being significantly cooler in the mouth than a sucrose solution of the same equivalent sweetness at the same temperature. This effect may be a wholly perceived organoleptic effect, it may involve an actual decrease in the temperature of the solution in the mouth or it may be due to a combination of these two possibilities. What is clear, however, is that the effect is unexpected because it cannot be due to heat of solution as the erythritol is already dissolved. Similar effects have been found with the other sugar alcohols xylitol, mannitol and sorbitol. However, these polyols are of less interest commercially since consumption at high concentration gives a laxative effect. This laxative effect is not observed with erythritol.

The perceived coolness of the beverage is important when refrigeration is absent. It is of even greater importance when the beverage (such as iced tea, soft drinks, fruit juices or any other beverage which is preferably intended for consumption at or below room temperature) is made by dissolving the erythritol, as a "powdered beverage" comprising flavours, prior to drinking because this will bring the temperature of the beverage down.

The compositions of the invention preferably comprise from 7.5 to 25% w/v erythritol. Above 25% w/v, the compositions become excessively sweet. The beverage compositions of the invention may be carbonated, by the addition of carbonated water to a pre-mix or by exposing the beverage to carbon dioxide at elevated pressures, for example, and are packaged in conventional ways such as in cans, bottles or, where the beverage is not carbonated, cartons or other sealed packages.

The beverage composition, which is ready-to-drink, is flavoured. Flavouring may occur by virtue of the natural flavours contained in the beverage, such as in iced tea or fruit juices, or by the addition of one or more natural or artificial flavours such as orange, lemon or cola, etc.. The composition may contain other conventional additives for beverages such as a preservative (e.g., sodium benzoate) and an intense sweetener such as aspartame, particularly when the drink is intended to be low in calories.

The oral care composition of the invention may be a mouth wash or a mouth rinse, for example, and may include conventional ingredients in this type of composition which are well-known to those skilled in the art. In particular, the compositions may contain cleansing, plaque inhibiting or antibacterial agents as well as solvents other than water. The erythritol in the composition aids its freshening effect.

The liquid pharmaceutical composition of the invention may be a cough syrup, for example. The composition may contain conventional pharmaceutical additives, carriers and excipients in addition to the pharmaceutically active substance.

The term "beverage composition" as used herein is intended to cover all liquid products which may be drunk including: carbonated and noncarbonated beverages such as soft drinks, fruit and/or vegetable based juices, lemonades, cordials, sport drinks, nut based drinks, tea, coffee; alcoholic drinks such as wine, beer, sake, cocktails, liqueurs; dairy products such as milk, whey and yoghurt and drinks based on them.

As mentioned above, the composition of the invention may be formed by the addition of water or another aqueous liquid (optionally carbonated) to a "powder" comprising erythritol and other additives. Alternatively, the solution may be formed by the dilution of a concentrate (or pre-mix) with water or another aqueous liquid (again, optionally carbonated), as described in EP-A-0759273, for example.

The following non-limiting examples illustrate the present invention.

EXAMPLE 1

Erythritol (19.0 g) was dissolved in still mineral water (100 ml) to give a 19% w/v solution. This solution was identified as having a sweetness equivalent to a 10% w/v solution of sucrose (i.e., a 10% SEV) and a sucrose solution of this latter concentration was also prepared.

Eleven female panellists took part in a study to assess the equivalent temperature difference that occurs in the mouth due to the cooling effect of the erythritol in solution compared to the sucrose solution.

The erythritol solution was stored at 20° C. overnight and part of the sucrose solution was stored at 2° C. and another part at 20° C. overnight before tasting.

Samples were portioned in 20 ml aliquots in plastic pots coded with random three-digit numbers.

Sensory testing was carried out in a purpose-built sensory evaluation laboratory using individual booths, under clear filter lights and at a temperature of approximately 22° C. Basic instructions, data acquisition and collection were monitored through a computerised data acquisition system, TASTE (Reading Scientific Services, Reading, UK). Solutions were assessed at 20° C., with panellists being given a brief outline of the objectives of the work, but no information on the nature of the solutions. Samples were assessed in triplicate using a sip-and-spit procedure. Panellists were asked to take all 20 ml of sample into their mouths as the volume of sample assessed would be crucial to the assessment of cooling effect, a small volume being likely to warm quickly in the mouth. Samples were presented in sets of three over four sessions in a semi-balanced design. Panellists evaluated coolness of the solution using an unstructured line scale with warm and cool being the extreme ends of the scale. The scale was anchored using a 20° C. 10% sucrose solution as the "warm" reference and a 5° C. 10% sucrose solution (the solution which was stored at 2° C. overnight) as the "cool" reference. The anchoring solutions were presented to the panel at the beginning of the morning and also tasted by the panel at the beginning of each session. Panellists had a 10–15 minute break between sessions to cut down the effects of fatigue. Still mineral water and crackers were used as palate cleansers during sessions and fresh carrot sticks and sparkling water were available as palate cleansers between sessions.

Cooling scores were averaged across panellists. Analysis of variance (ANOVA) was carried out to explore differences between samples. A mean cooling score of 40.3 was obtained for the erythritol solution and this was then converted to the corresponding solution temperature of 14° C., on the line scale using 5° C. and 20° C. as the extreme ends of the scale. A numerical score on the unstructured line scale could be converted to a "temperature score" by making the assumption that the scale extends linearly over 15° C., from 20° C. to 5° C. The conclusion from this experiment is that a 20° C. solution of erythritol at 10% SEV was found to have a similar cooling effect to a sucrose solution at 14° C.

Panellists were able to assess the cooling effect of erythritol in solution as a temperature effect in the mouth using the methodology described above.

It is clear from these results that a beverage having a cooling effect can be prepared using erythritol at concentrations of more than 7% w/v.

EXAMPLE 2

Example 1 was repeated using erythritol solutions of different concentrations from 7.3 to 19.0 g/ml. The results are given in Table 1.

TABLE 1

Effect of Erythritol at Different Concentrations

| Concentration of Erythritol | | Temperature Equivalence |
|---|---|---|
| % SEV | g/100 ml | ° C. |
| 4 | 7.3 | 13.6 |
| 6 | 11.2 | 14.5 |
| 8 | 15.1 | 14.6 |
| 10 | 19.0 | 14.6 |

Thus, the cooling effect of erythritol in aqueous solution was observed throughout the range of concentrations tested.

What is claimed is:

1. A packaged, ready-to-drink, flavored liquid beverage composition selected from the group consisting of a soft drink, fruit juice and ice tea, said packaged, ready-to-drink, flavored liquid beverage composition containing from 15.1% to 25% w/v erythritol, and wherein said liquid beverage composition provides a cooling sensation when taken orally by a consumer.

2. A packaged, ready-to-drink flavored beverage composition according to claim 1, wherein said liquid beverage composition is carbonated.

3. A packaged, ready-to-drink flavored beverage composition according to claim 2, said liquid beverage composition additionally containing an intense sweetener.

* * * * *